United States Patent
Skogo et al.

(10) Patent No.: US 9,179,838 B2
(45) Date of Patent: Nov. 10, 2015

(54) EYE/GAZE TRACKER AND METHOD OF TRACKING THE POSITION OF AN EYE AND/OR A GAZE POINT OF A SUBJECT

(71) Applicant: Tobii Technology AB, Danderyd (SE)

(72) Inventors: Marten Skogo, Danderyd (GB); Henrik Jonsson, Stockholm (SE); John Elvesjo, Stockholm (SE)

(73) Assignee: Tobii Technology AB, Danderyd (SE)

( * ) Notice: Subject to any disclaimer, the term of this patent is extended or adjusted under 35 U.S.C. 154(b) by 67 days.

(21) Appl. No.: 14/201,171

(22) Filed: Mar. 7, 2014

(65) Prior Publication Data
US 2014/0268055 A1    Sep. 18, 2014

(30) Foreign Application Priority Data

Mar. 15, 2013  (GB) .................................. 1304885.5

(51) Int. Cl.
| | |
|---|---|
| A61B 3/14 | (2006.01) |
| A61B 3/00 | (2006.01) |
| A61B 3/113 | (2006.01) |
| G06F 3/01 | (2006.01) |
| G06K 9/00 | (2006.01) |

(52) U.S. Cl.
CPC ................ *A61B 3/113* (2013.01); *G06F 3/013* (2013.01); *G06K 9/00604* (2013.01)

(58) Field of Classification Search
USPC ................................................ 351/200–246
See application file for complete search history.

(56) References Cited

U.S. PATENT DOCUMENTS

| | | |
|---|---|---|
| 5,861,940 A | 1/1999 | Robinson et al. |
| 6,201,233 B1 | 3/2001 | Shiono |
| 6,252,977 B1 | 6/2001 | Salganicoff et al. |
| 6,959,102 B2 | 10/2005 | Peck |
| 2007/0097349 A1 | 5/2007 | Wada et al. |
| 2013/0026384 A1 | 1/2013 | Kim et al. |
| 2013/0044247 A1 | 2/2013 | Kawahito et al. |
| 2013/0120712 A1* | 5/2013 | Spasovski ...................... 351/209 |
| 2015/0131051 A1* | 5/2015 | Huang ........................... 351/206 |

FOREIGN PATENT DOCUMENTS

| | | |
|---|---|---|
| EP | 2519001 A2 | 10/2012 |
| WO | 2004045399 A1 | 6/2004 |
| WO | 2013036632 A1 | 3/2013 |

* cited by examiner

*Primary Examiner* — Mohammed Hasan
(74) *Attorney, Agent, or Firm* — Moore & Van Allen PLLC; W. Kevin Ransom

(57) ABSTRACT

An eye/gaze tracker with first and second light sources each configured to illuminate an eye of a subject and controlled to selectively emit light towards the eye in such a manner that within an operation sequence the eye is illuminated by the first light source during at least one first interval and by the second light source during at least one second interval. An image sensor has a plurality of photodiodes each of which is associated with first and second charge storages configured to store electric charges based on an amount of light reaching the photodiode. At least one switch of the image sensor is controlled such that the electric charges are stored in the first charge storage as a result of the illumination during the at least one first interval and in the second charge storage as a result of the illumination during the at least one second interval.

21 Claims, 4 Drawing Sheets

EYE/GAZE TRACKER AND METHOD OF TRACKING THE POSITION OF AN EYE AND/OR A GAZE POINT OF A SUBJECT

CROSS-REFERENCE TO RELATED APPLICATION

This application claims priority to foreign application Great Britain 1304885.5 filed Mar. 15, 2013, the contents of which are hereby incorporated by reference herein.

FIELD OF THE INVENTION

The present invention relates generally to reliable tracking of a subject's eyes and/or gaze point.

BACKGROUND OF THE INVENTION AND PRIOR ART

High-performance eye tracking systems often use active illumination of a subject's eyes. This typically means that one or more light sources emit near-infrared light and one or more cameras capture images of the illuminated eyes. In the captured images, various features are extracted, such as the specular reflections of the illumination light source on the cornea (so-called glints) and/or the position of the pupil relative to the position of the eye.

There are two principal illumination strategies, which differ in how the pupil appears in the captured images. If the light source is located close to the camera, in the resulting image the pupil will typically be represented by image elements associated with a relatively bright signal level compared to the surrounding iris. If, instead, the light source is located further away from the camera, the pupil will normally appear comparatively dark in the captured images. This is referred to as bright pupil (BP) imaging and dark pupil (DP) imaging respectively.

For some people, the contrast between iris and pupil, and hence the stability of the eye tracking algorithms, may be optimal in BP mode and for other people, that lack a distinct bright-pupil effect, DP images will have the best contrast. Since an automatic eye/gaze tracker cannot know beforehand whether a particular subject belongs to the former or latter category, it is an advantage if the system is capable of capturing both BD and DP images. This, in turn, however, requires either two cameras or the capture of two images which are separated in time. The former alternative is associated with costs and technical complexity, whereas the latter suffers from motion-related errors.

Further, in some implementations, it may be advantageous to use more than one light source being physically separated from one another to obtain two or more glint signals on the image of the eye. Namely, this, in combination with the known geometry of how the camera and light sources are arranged in the eye/gaze tracker components, can be used to calculate both the radius of the cornea and the distance to the eye. However, simultaneous illumination from two or more light sources is problematic because it may result in a hybrid DP/BP effect in the registered images. This causes a poor pupil/iris contrast. Moreover, if the glints are located too close to one another with respect to the available resolution (due to limited optical performance, the size of the pixels or a combination thereof), the glints will blend into each other. This causes inaccuracy when determining the center-of-glint-positions. Additionally, such intermixed glints may obscure the pupil edge, which must be visible for accurate eye tracking algorithms.

U.S. Pat. No. 6,959,102 describes a method for increasing the signal-to-noise ratio in infrared-based eye gaze trackers used in the presence of ambient light, such as sunlight. Here, an infrared illuminator is modulated in synchronicity with a camera, such that for example, a first frame contains both the illuminator signal and the ambient radiation information, and a second frame contains only the ambient radiation information. Thus, given that the variation in the ambient radiation is slow, it is possible to subtract the ambient radiation information from the image data of the first frame, and thereby the eye/gaze tracking can be improved.

EP 2 519 001 discloses another solution for determining the ambient radiation contribution to a scene. Here, a stream of light pulses periodically illuminates the scene. Light reflected from the scene is registered in such a manner that during a light pulse electric charges originating from the incoming light are stored in a first storage element of a pixel in an image sensor; and between the light pulses, electric charges originating from the incoming light are stored in a second storage element of the same pixel.

Consequently, there are solutions for reducing the influence from ambient light, e.g. the sun, which may generate patterns and/or reflections disturbing the eye tracking algorithms and deteriorating the eye tracker performance. However, as discussed above, several additional problems must also be addressed to improve the tracking robustness of the eye/gaze tracker.

SUMMARY OF THE INVENTION

The object of the present invention is to mitigate the above problems, and thus offer a robust eye/gaze tracking solution for a wide range of subjects irrespective of their ethnicity and the environment in which the eye/gaze tracker is used.

According to one aspect of the invention, the object is achieved by the initially described eye/gaze tracker, wherein the image registering means includes an image sensor with a plurality of photodiodes. Each photodiode is here associated with first and second charge storages configured to store electric charges based on an amount of light reaching the photodiode. One or more switches are controllable to cause the electric charges to be stored in the first charge storage or the second charge storage. The control unit is configured to control the light sources to selectively emit light towards the eye in such a manner that, within an operation sequence, the eye is illuminated by the first light source during at least one first interval and by the second light source during at least one second interval. Alternatively, the image sensor may be configured to control the light sources in this manner, i.e., the control unit may be partially integrated across the image sensor and external, or integrated directly with the image sensor. In any case, the control unit is further configured to control the switch(es) such that the electric charges are stored in the first charge storage as a result of the illumination during the at least one first interval and in the second charge storage as a result of the illumination during the at least one second interval. The eye/gaze tracker also includes a data processor that is configured to process image data recorded by the image registering means. The image data have been registered when the eye is illuminated by light from one of the light sources. Based on the image data, the data processor is configured to generate an output signal describing a position of the eye and/or a gaze point for the eye.

This eye/gaze tracker is advantageous because it provides simultaneous illumination from more than one light source without risking any undesired effects resulting from the interference between the light from the different light sources. Thus, high-quality eye/gaze tracking is enabled.

According to one preferred embodiment of this aspect of the invention, the data processor is configured to process image data that have been registered when the eye is illuminated by light from two (or all) of the light sources, and based thereon generate the output signal Hence, a high-quality output signal is obtained, which may be used for a wide range purposes, e.g. to control a computer.

According to another preferred embodiment of this aspect of the invention the data processor is configured to derive an image quality metric describing a quality level of the image data recorded in a given interval of the at least one first or second interval. Here, the control unit is configured to produce the output signal exclusively based on image data having an image quality metric exceeding a predetermined quality threshold. Thereby, the output signal can be kept free from the influence of poor-quality eye-tracking data.

According to yet another preferred embodiment of this aspect of the invention the eye/gaze tracker contains a third light source in addition to the first and second light sources. The third light source is likewise configured to illuminate the eye of the subject. The control unit is configured to control the light sources to selectively emit light towards the eye in such a manner that within an operation sequence the eye is illuminated by the first light source during the at least one first interval, and by one of the second and third light sources during at least one second interval. The control unit is also configured to control the switch(es) such that the electric charges are stored in the first charge storage as a result of the illumination during the at least one first interval and in the second charge storage as a result of the illumination during the at least one second interval. In other words, a subset of the light sources is used to generate the image data. Preferably, the subset is selected so that one or more quality-related parameters are optimized. For example, the active subset of the light sources may be selected based on an image quality metric, such that only light from the light sources being associated with a highest image quality is used at each occasion. In fact, according to the invention, this principle may be extended to a general case, such that whenever the number of light sources exceeds the number of charge storages associated with each photodiode of the image sensor, a subset of light sources is selected, which subset contains a number of light sources equal to the number of charge storages associated with each photodiode.

According to still another preferred embodiment of this aspect of the invention the control unit is configured to illuminate the eye and register the image data according to a periodic scheme. This scheme defines a respective sequence of illumination intervals when each of the light sources shall be active and passive respectively. Thus, an operation routine for the image registering means is synchronized to the sequence of illumination intervals, such that a first portion of the image data recorded when the eye is illuminated by the first light source is separated from a second portion of the image data recorded when the eye is illuminated by the second light source.

Preferably, referring to the general case above, the periodic scheme defines a sequence of illumination intervals including as many different categories of intervals as there are charge storages associated with each photodiode. This means that a subject's eye can be essentially simultaneously illuminated by light from a large number of light sources without risking that the different light sources interfere with one another in a counter-productive manner.

According to a further preferred embodiment of this aspect of the invention the periodic scheme specifically defines a first sequence of illumination intervals during which the first light source shall be active, and a second sequence of illumination intervals during which the second light source shall be active. The first sequence of intervals is here temporally interleaved with the second sequence of intervals. Moreover, the control unit is configured to read out the image data after that at least one of the light sources has been activated at least two times. In other words, a first image is generated based on light from one light source which is collected during periods in between which light is emitted, which serves as a basis for a second image. Thereby, the first and second images can be regarded as representing the same time instance.

Preferably, the operation sequence corresponds to the exposure time for one standard frame of a moving-image sequence recorded by the image registering means. This means that, if two light sources are used, two essentially simultaneously registered images are produced, which each is exposed during half the duration of one standard frame.

According to yet a further preferred embodiment of this aspect of the invention, the light sources are arranged at a distance to the image registering means and a stipulated operating distance between the eye/gaze tracker and the eye, such that the light emitted from each of the light sources is expected to cause a dark-pupil effect in the image data representing the eye. Hence, efficient DP-based eye/gaze tracking is enabled also in situations where a conventional DP-tracker would fail for example due to unfortunate reflections in a subject's spectacles.

According to another preferred embodiment of this aspect of the invention a first light source is arranged at a distance to the image registering means and a stipulated operating distance between the eye/gaze tracker and the eye, such that the light emitted from the first light source is expected to cause a bright-pupil effect in the image data representing the eye; and a second light source of the light sources is arranged at a distance to the image registering means and a stipulated operating distance between the eye/gaze tracker and the eye, such that the light emitted from the second light source is expected to cause a dark-pupil effect in the image data representing the eye. This arrangement is advantageous because it facilitates automatic selection between BP or DP operation depending on which is more efficient for the subject in question.

According to still another preferred embodiment of this aspect of the invention a first light source of the light sources is configured to emit light at a first center wavelength, and a second light source of the at least two light sources is configured to emit light at a second center wavelength which is separated from the first center wavelength by at least 60 nm. Thus, the first and second light sources may for example emit light at around 850 nm and 940 nm respectively, where due to absorption differences in the water molecule, the former wavelength is prone to cause a BP-effect, whereas the latter more probably causes a DP-effect.

Preferably, the first and second light sources are implemented in a common illuminator unit, which is tunable in response to a wavelength control signal so as to generate both the light at the first center wavelength and the light at the second center wavelength. The control unit is further arranged to generate the wavelength control signal and provide the common illuminator with this signal, such that the common illuminator unit is caused to generate light at the first center wavelength during the at least one first interval and generate light at the second center wavelength during the at least one second interval. Consequently, a highly compact and uncomplicated design is attained.

According to other aspects of the invention, the object is achieved by the portable computing device and the motor vehicle respectively described initially each into which the proposed eye/gaze tracker is integrated. These entities are associated with the same advantages as discussed above referring to the proposed eye/gaze tracker.

According to another aspect of the invention, the object is achieved by the method described initially, wherein the image registering means is presumed to have an image sensor with a plurality of photodiodes each of which is associated with first and second charge storages configured to store electric charges based on an amount of light reaching the photodiode.

Further, at least one switch is controllable to cause the electric charges to be stored in the first charge storage or the second charge storage. The method involves controlling the light sources to selectively emit light towards the eye in such a manner that, within an operation sequence, the eye is illuminated by the first light source during at least one first interval and by the second light source during at least one second interval. The method also involves controlling the at least one switch, such that the electric charges are stored in the first charge storage as a result of the illumination during the at least one first interval and in the second charge storage as a result of the illumination during the at least one second interval. The image data recorded by the image registering means when the eye was illuminated by light from one of the light sources are processed. Based thereon, an output signal is generated, which describes a position of the eye and/or a gaze point for the eye. The advantages of this method, as well as the preferred embodiments thereof, are apparent from the discussion above with reference to the proposed eye/gaze tracker.

According to a further aspect of the invention the object is achieved by a computer program product, which is loadable into the memory of a computer, and includes software adapted to implement the method proposed above when said computer program product is run on a computer.

According to another aspect of the invention the object is achieved by a computer readable medium, having a program recorded thereon, where the program is to control a computer to perform the method proposed above when the program is loaded into the computer.

Further advantages, beneficial features and applications of the present invention will be apparent from the following description and the dependent claims.

BRIEF DESCRIPTION OF THE DRAWINGS

The invention is now to be explained more closely by means of preferred embodiments, which are disclosed as examples, and with reference to the attached drawings.

DESCRIPTION OF PREFERRED EMBODIMENTS OF THE INVENTION

Figures 1, 4A, 4B, 5A, 5B, 5C:
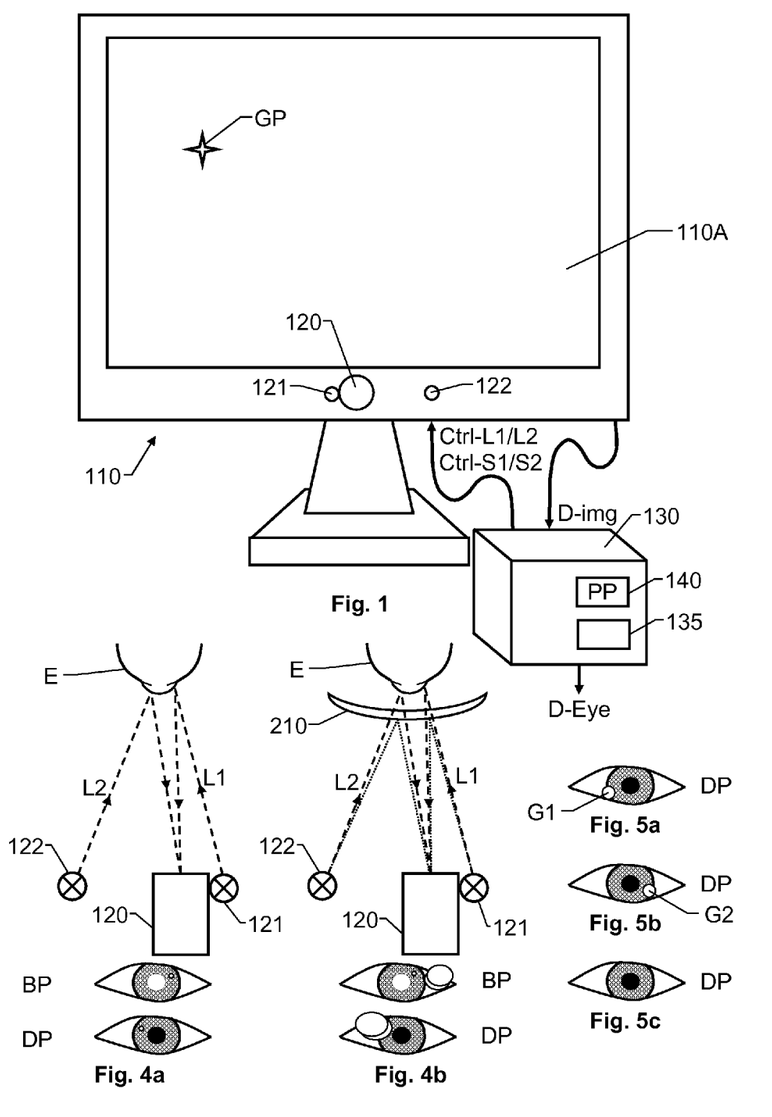
FIG. 1 shows an eye/gaze tracker according to a first embodiment of the invention.
FIGS. 4*a-b* illustrate the BP- and DP-effect for a subject without and with glasses respectively.
FIGS. 5*a-c* illustrate how the pupil edge of an eye may be reconstructed based on dual imaging according one embodiment of the invention.

FIG. 1 shows an eye/gaze tracker according to a first embodiment of the invention. The eye/gaze tracker includes first and second light sources 121 and 122 respectively, an image registering means 120 and a control unit 130.

Each of the first and second light sources 121 and 122 is configured to illuminate an eye E of a subject. The image registering means 120 is configured to record image data D-Img representing the eye E. The control unit 130 is configured to control the light sources 121 and 122 as well as the image registering means 120. The image registering means 120 contains an image sensor with a plurality of light sensitive elements, or pixels, which each is associated with a photodiode PD, and that are preferably arranged in a matrix, i.e. as a first number of columns and a second number of rows. For example, in a 5 megapixel sensor (having in total 5 090 816 light sensitive elements), the first number of columns may be 2 608 and the second number of rows may be 1 952. The image sensor may for example be implemented in CMOS or CCD technology (CMOS=complementary metal-oxide-semiconductor; CCD=charge-couple device).

Figure 3:
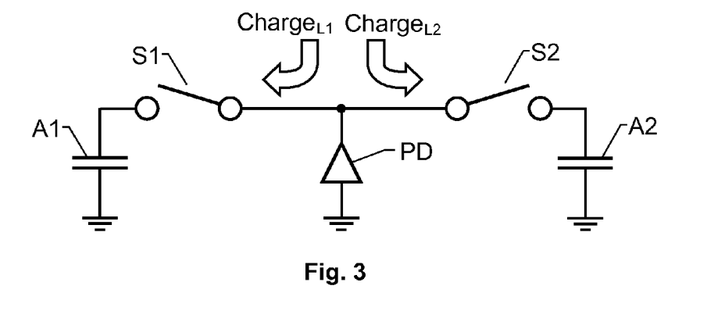
FIG. 3 shows a schematic view of a light sensitive element according to one embodiment of the invention.

FIG. 3 shows a schematic view of a light sensitive element according to one embodiment of the invention. The light sensitive element includes the photodiode PD, which allows electric charge to be accumulated in response to incoming light L1 or L2. Each photodiode PD, in turn, is associated with first and second charge storages A1 and A2 respectively, which are configured to store electric charge transferred from the photodiode PD.

Switches S1 and S2 respectively are controllable to cause the electric charge that has been temporarily stored on the photodiode PD to be transferred either to the first charge storage A1 or the second charge storage A2. Thus, only one of the switches S1 and S2 is closed at each point in time. Naturally, such a selective storage of charges in either one of the first and second charge storages A1 and A2 may alternatively be accomplished via a single two-stage switch instead of the switches S1 and S2 illustrated in FIG. 3.

In any case, via a first control signal Ctrl-L1/L2, the control unit 130 is configured to control the light sources 121 and 122 to selectively emit light L1 and L2 towards the eye E. Specifically, according to the invention, light L1 and L2 is emitted in such a manner that within an operation sequence, the eye E is illuminated by light L1 from the first light source 121 during at least one first interval and by light L2 from the second light source 122 during at least one second interval. Furthermore, via a second control signal Ctrl-S1/S2, the control unit 130 is configured to control the switches S1 and S2 such that electric charge from the photodiode PD is transferred to the first charge storage A1 during the at least one first interval, and to the second charge storage A2 during the at least one second interval.

Figure 2A:
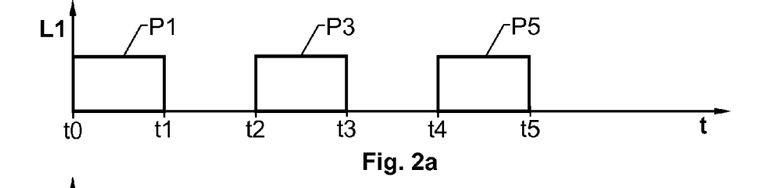
FIGS. 2*a-d* exemplify the illumination and image registering sequences according to one embodiment of the invention.

FIG. 2*a* shows a first graph exemplifying how the first light source L1 is activated within an operation sequence from t=t0 to t=t6. Specifically, the first light source L1 is here active during a first set of intervals P1, P3 and P5 extending from t0 to t1, from t2 to t3 and from t4 to t5 respectively.

Figure 2B:
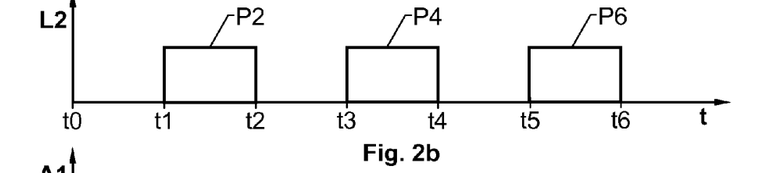

FIG. 2*b* shows a second graph exemplifying how the second light source L2 is activated within the operation sequence t=t0 to t=t6. Specifically, the second light source L2 is active during a second set of intervals P2, P4 and P6 extending from t1 to t2, from t3 to t4 and from t5 to t6 respectively.

Thus, as can be seen, the first and second sets of intervals P1, P3, P5 and P2, P4, P6 are non-overlapping. According to the invention, temporally overlapping illumination intervals are also conceivable. However, to simplify the image data processing, it is preferable if the image registering means 120 is configured to exclusively record the image data D-Img when only one of the light sources L1 or L2 is active.

Figure 2C:
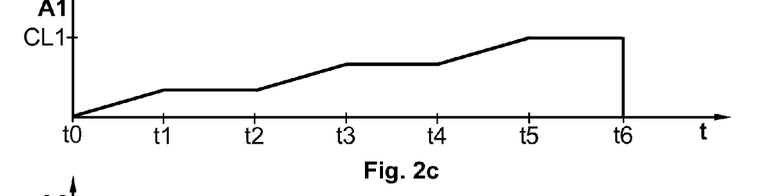
Figure 2D:
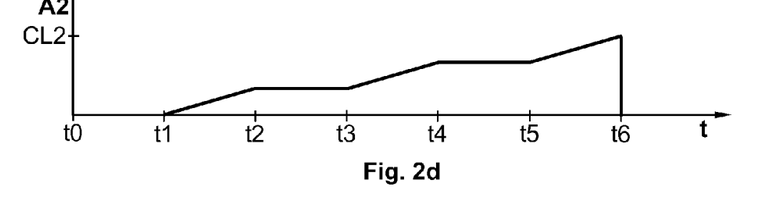

FIG. 2c shows a graph illustrating how electric charge is accumulated in the first charge storage A1 as a function of time t, and analogously, FIG. 2d shows a graph illustrating the accumulation of electric charge in the second charge storage A2 as a function of time t. In the first charge storage A1, charges are stored whenever the first light source L1 is active, i.e. in connection with the first interval P1 from t0 to t1, the third interval P3 from t2 to t3 and in connection with the fifth interval from t4 to t5. Thus, at t=t5, the electric charge in the first charge storage A1 reaches a final value of CL1.

Analogously, charges are stored in the second charge storage A2 whenever the second light source L2 is active, i.e. in connection with the second interval P2 from t1 to t2, the fourth interval P4 from t3 to t4 and in connection with the sixth interval from t5 to t6, so that at t=t6, the electric charge in the second charge storage A2 reaches a final value of CL2. Given uniform ambient light conditions and that all the intervals P1, P2, P3, P4, P5 and P6 have an equal extension in time, CL1 will be equal to CL2; assuming that the image was captured in an integrating sphere or imaging some other form of uniform reflector.

FIGS. 2c and 2d thus illustrate that charge is accumulated at the charge storages A1 and A2 respectively. This means that the switches S1 and S2 are open during the whole respective intervals. An alternative is to have the switches S1 and S2 opened only for a short period at the end of each respective interval. This embodiment of the invention is described below referring to FIG. 9.

The extension in time for the operation sequence t0 to t6 preferably corresponds to a standard exposure time for one frame of a moving-image sequence recorded by the image registering means 120.

Preferably, the control unit 130 is configured to cause the eye E to be illuminated and corresponding the image data D-Img to be registered according to a periodic scheme, which defines a respective sequence of illumination intervals P1, P3, P5 and P2, P4, P6 when each of the light sources 121 and 122 respectively shall be active or passive. An operation routine for the image registering means 120 is synchronized to the sequences of illumination intervals P1, P3, P5 and P2, P4, P6, such that a first portion of the image data D-Img recorded when the eye E is illuminated by the first light source 121 is separated from a second portion of the image data D-Img recorded when the eye E is illuminated by the second light source 122.

The periodic scheme may define a first sequence of illumination intervals P1, P3 and P5 during which the first light source 121 shall be active, and a second sequence of illumination intervals P2, P4 and P6 during which the second light source 122 shall be active. The first sequence of intervals P1, P3 and P5 is here temporally interleaved with the second sequence of intervals P2, P4 and P6. The control unit 130 is configured to read out the image data D-Img only after that at least one of the light sources 121 and 122 has been activated at least two times. Otherwise, there is no temporal interleaving.

Returning now to FIG. 1, according to one embodiment of the invention, the eye/gaze tracker includes a data processor 135. This unit is configured to process image data D-Img recorded by the image registering means 120, which image data D-Img have been registered when the eye E is illuminated by light from one of the light sources 121 and 122. Based thereon, the data processor 135 is configured to generate an output signal D-Eye describing a position of the eye E and/or a gaze point GP for the eye E, for instance on an active area 110A of the display unit 110 into which the eye/gaze is integrated.

Preferably, the data processor 135 is also configured to derive an image quality metric describing a quality level of the image data D-Img recorded in a given interval P1, P2, P3, P4, P5 or P6 respectively. The control unit is further configured to produce the output signal D-Eye (e.g. representing eye/gaze data) exclusively based on image data D-Img having an image quality metric exceeding a predetermined quality threshold. Thus, it can be avoided that eye/gaze data D-Eye is calculated based on poor/unreliable image data D-Img.

FIG. 4a illustrates a design of the eye/gaze tracker, where the first light source 121 is arranged at a distance to the image registering means 120 and a stipulated operating distance between the eye/gaze tracker and the eye E, such that the light L1 emitted from the first light source 121 is expected to cause a brightpupil effect in the image data D-Img representing the eye E. In practice, this is equivalent to locating the first light source 121 as close as possible to the image registering means 120.

The second light source 122 is here arranged at a distance to the image registering means 120 and a stipulated operating distance between the eye/gaze tracker and the eye E, say 45 cm to 100 cm, such that the light L2 emitted from the second light source 122 is expected to cause a dark-pupil effect in the image data D-Img representing the eye E. This typically means that the distance between the image registering means 120 and the second light source 122 is around 3 cm to 60 cm.

Depending on which set of the image data D-Img that provides a strongest contrast between the pupil and the cornea, the eye/gaze data D-Eye may be based on the image data recorded when the eye E is illuminated by the first or second light source 121 or 122. Of course, if both sets provide sufficient contrast, no image data D-Img need to be discarded.

FIG. 4b illustrates the same eye/gaze-tracker design as FIG. 4a. Here, however, the subject wears glasses 210. This causes additional reflections in the image data D-Img. Assuming that these reflections only overlap with the pupil edge in the images of the eye E due to the light L2 from the second light source 122, it is generally preferable to calculate the eye/gaze data D-Eye based exclusively on the image data D-Img recorded when the eye E is illuminated by the first light source 121. Namely, to attain high accuracy, the eye tracking algorithms normally require that the pupil edge is visible. Hence, other factors than the pupil-cornea contrast may determine which light source 121 or 122 is preferable.

Nevertheless, as mentioned above, according to the invention, it is not necessary to select one set of the image data D-Img registered when one of the light sources 121 or 122 is active (or a subset of the image data D-Img registered when a subset of the light sources is active). Instead, under certain circumstances, it is preferable if the eye/gaze data D-Eye are calculated based on all the registered image data D-Img.

For example, referring to FIG. 5a, in a first image registered when a first light source 121 is active, a first part of the pupil edge of a subject's eye may be obscured by a first glint G1. In a second image (see FIG. 5b) registered when a second light source 122 is active, a second part of the pupil edge may be obscured by a second glint G2. This is simply the result of that the position of the glint changes when a different light source is active. Since both images are captured by the image registering means 120 with the same pixel geometry and also essentially simultaneously (or in a temporally interleaved manner as described above), the images have a perfect geometric matching. Consequently, the pupil edge points in the first image can be directly combined with the pupil edge points calculated from the second image. This is illustrated in FIG. 5c. To finally calculate pupil ellipse parameters, pupil points from both the first and second images may therefore be used. In fact, a substantial benefit of doing so is that a larger portion of the pupil edge will thereby have correctly calculated data points. As a result, an ellipse fitting of the eye-tracking algorithm will be improved significantly.

Additionally, non-uniform lighting may cause shading across the pupil, which may introduce small errors in the pupil calculations. Using two or more illumination sources as described above may reduce this undesired effect substantially.

Furthermore, when comparing said two images, it is also straightforward to identify any reflections caused by ambient light sources. Namely, such reflections are present at the same locations in both images. A more robust eye tracker may thus be attained by identifying and removing disturbances from ambient light sources.

According to one embodiment of the invention, two or more of the light sources are arranged at such respective distances to the image registering means 120 and a stipulated operating distance between the eye/gaze tracker and the eye E, such that the light L1 and L2 respectively emitted from each of the light sources is expected to cause a dark-pupil effect in the image data D-Img representing the eye E. For example, any undesired reflections may thereby be avoided without having disregard image data which otherwise is of good quality, e.g. with respect to pupil-cornea contrast.

Figures 6, 7:
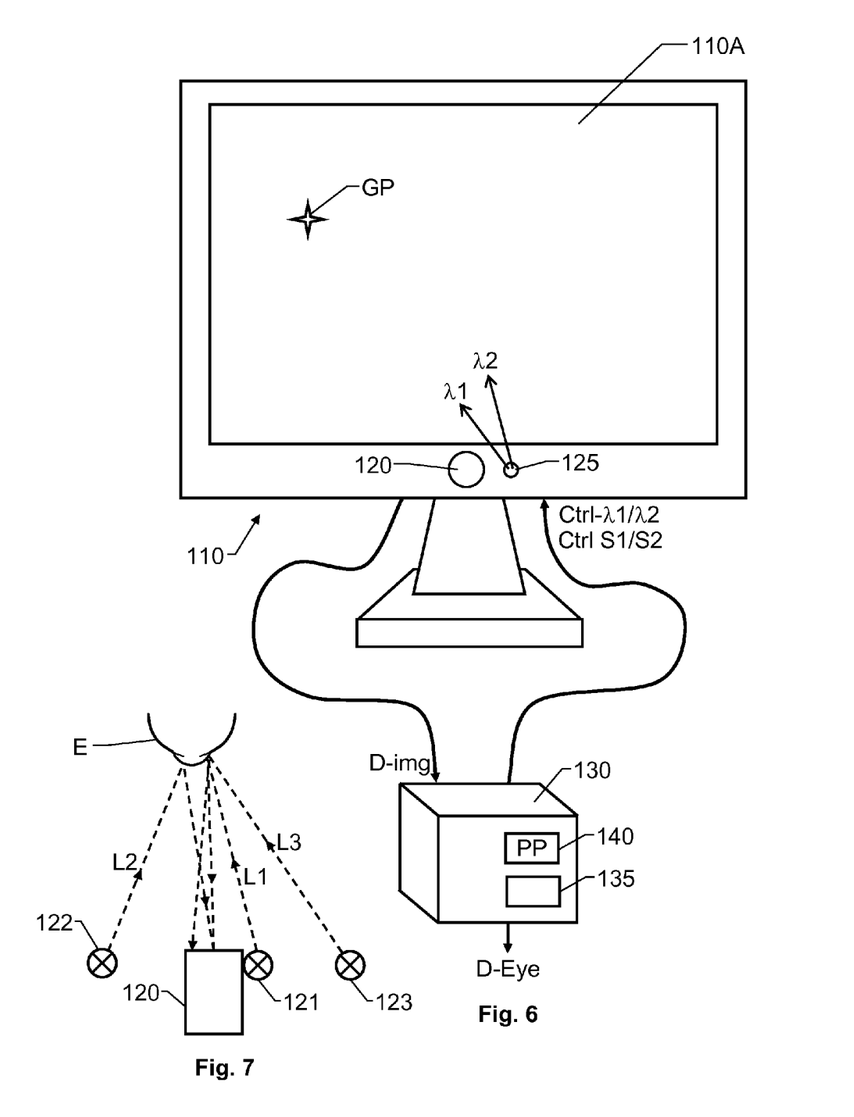
FIG. 6 shows an eye/gaze tracker according to a second embodiment of the invention.
FIG. 7 illustrates how the eye of a subject may be illuminated by multiple light sources according to one embodiment of the invention.

FIG. 7 illustrates how the eye E of a subject is illuminated by a first light source 121 arranged close to the image registering means 120 and by second and third light sources 122 and 123 respectively, which are arranged at such respective distances to the image registering means 120 and a stipulated operating distance between the eye/gaze tracker and the eye E, such that the light L2 and L3 respectively emitted from each of the light sources 122 and 123 is expected to cause a dark-pupil effect in the image data D-Img representing the eye E.

In this case, the control unit 130 is configured to control the light sources 121, 122 and 123 to selectively emit light L1, L2 and L3 respectively towards the eye E in such a manner that within an operation sequence, the eye E is illuminated by the first light source 121 during the at least one first interval, and by one of the second and third light sources 122 or 123 during at least one second interval. Preferably, the selection between the second and third light sources 122 and 123 is based on an image-quality related parameter, such as whether or not a particular light source is associated with quality deteriorating reflections and/or poor contrast. Naturally, the control unit 130 need not select between the second and third light sources 122 and 123, however it may equally well select between any other pair of light sources.

In any case, the control unit 130 is configured to control the switches S1 and S2 such that the electric charges are stored in the first charge storage A1 in connection with the at least one first interval and in the second charge storage A2 in connection with the at least one second interval.

The invention may be extended to a general case with any number of light sources larger than or equal to two, and any number larger than or equal to two of charge storages associated with each photodiode PD of the image sensor. If the number of light sources exceeds the number of charge storages associated with each photodiode, the control unit 130 is configured to select a subset of light sources, which subset contains a number of light sources equal to the number of charge storages associated with each photodiode PD.

FIG. 6 shows an eye/gaze tracker according to a second embodiment of the invention, wherein a common illuminator unit 125 implements both a first light source and a second light source. The first implemented light source is configured to emit light L1 at a first center wavelength $\lambda 1$ and the second implemented light source is configured to emit light L2 at a second center wavelength $\lambda 2$ which is separated from the first center wavelength $\lambda 1$ by at least 60 nm. Thus, the first light source may emit light at around 850 nm and the second light source may emit light at around 940 nm.

The common illuminator unit 125 is tunable, so that, in response to a wavelength control signal Ctrl-$\lambda 1/\lambda 2$ it generates either the light L1 at the first center wavelength $\lambda 1$ or the light L2 at the second center wavelength $\lambda 2$. Furthermore, the control unit 130 is arranged to generate the wavelength control signal Ctrl-$\lambda 1/\lambda 2$ such that the common illuminator unit 125 is caused to generate light L1 at the first center wavelength $\lambda 1$ during at least one first interval, say P1, P3 and P5; and generate light L2 at the second center wavelength $\lambda 2$) during at least one second interval, say P2, P4 and P6.

As an alternative to a truly common unit, the common illuminator 125 may be implemented as two physically separate illuminators configured to emit light at different wavelengths, which are placed closely together. By "closely together" is here understood, so close to one another that the illuminators' centers of illumination as seen from the eye E is less than two degrees apart in gaze angle.

Preferably, the data processing device 130 contains, or is in communicative connection with a memory unit 140 storing a computer program product PP, which contains software for controlling the data processing unit 130 to perform the above-described actions when the computer program product PP is run on the data processing device 130.

The proposed eye/gaze tracker may be incorporated in a wide range of entities, and thus enhance the user-friendliness and reliability thereof. For example, the eye/gaze tracker may be included in battery operated equipment in the form of a portable computing device, such as a laptop PC, a tablet computer, an ultrabook or a smart phone. However, the eye/gaze tracker may equally well be integrated into a motor vehicle, such as a car, motorcycle or truck for example to detect driver drowsiness and/or to control various functions in the vehicle.

Figure 8:
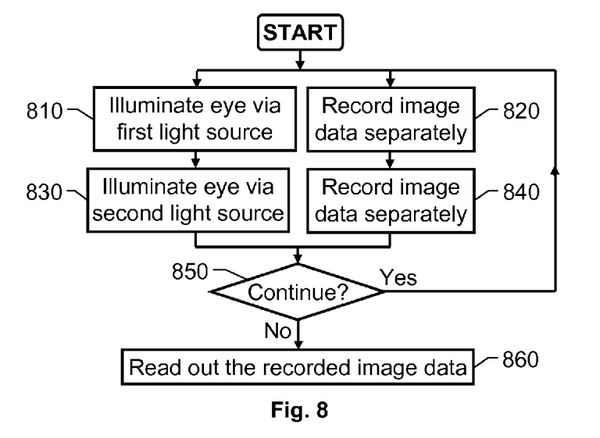
FIG. 8 illustrates, by means of a flow diagram, the general method according to the invention.

To sum up, we will now describe the proposed operation sequence of the eye/gaze tracker according to the invention with reference to the flow diagram in FIG. 8.

In a first step 810, a first light source illuminates at least one eye of a subject. In parallel, a step 820 records image data representing the at least one eye. Specifically, electric charges are stored in a first charge storage in response to an amount of light received when the first light source is active. Subsequently, i.e. after completing a first illumination interval, in a step 830, a second illumination interval is initiated, wherein a second light source illuminates the at least one eye. In parallel, a step 840 records image data representing the at least one eye by storing electric charges in a second charge storage in response to an amount of light received when the second light source is active. After that, a step 850 checks whether the image recording is completed. Preferably, the image recording involves at least two iterations for at least one of the illuminator/charge-storage pairs. Thus, after a first run-through of steps 810 to 840, it is desirable if the procedure loops back from step 850 to steps 810 and 820 for continued recording of image data.

Nevertheless, after completing an operation sequence involving a set of first and second intervals during which the first and second light sources are active respectively, a step 860 follows after step 850. In step 860, the recorded image data are read out for further processing in order to derive eye/gaze data there from. The image data, as such, may be represented by two separate images captured with the light L1 and L2 from the first and second light sources 121 and 122 respectively. Alternatively, the image data may be represented by a difference image between said separate images.

Figure 9:
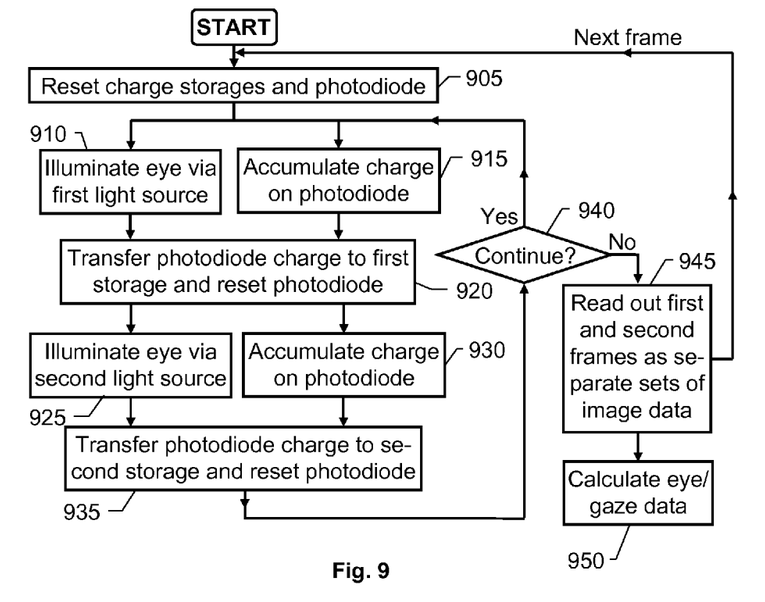
FIG. 9 shows flow diagram illustrating an embodiment of the method according the invention.

FIG. 9 contains another flow diagram, which illustrates the method according to one embodiment of the invention with further reference to FIGS. 1, 2a-2d and 3.

In a first step 905, the first charge storage A1, the second charge storage A2 and the photodiode PD are all reset. Then, in a step 910, analogous to the above, the first light source 121 illuminates the eye E with light L1 during a first interval P1. In a parallel step 915, electric charges are accumulated on the photodiode PD of each image element in the image sensor in response to the amount of light that reaches that image element.

Upon expiry of the first interval P1, i.e. at t=t1, the charge accumulated on the photodiode PD is transferred to the first charge storage A1 in a step 920. Thereafter, the photodiode PD is reset.

Then, as of t=t1, follows a step 925 in which the second light source 122 illuminates the eye E with light L2 during a second interval P2. In parallel, a step 930 accumulates electric charges on the photodiode PD of each image element in the image sensor in response to the amount of light that reaches that image element.

Upon expiry of the second interval P2, i.e. at t=t2, the charge accumulated on the photodiode PD is transferred to the second charge storage A2 in a step 935. Thereafter, the photodiode PD is reset.

Subsequently, a step 940 checks whether the operation sequence includes any additional first or second intervals. If so, the procedure loops back to steps 910 and 915. Otherwise, a step 845 follows in which first and second image frames are read out as separate sets of image data D-Img from the first and second charge storages A1 and A2 respectively, or as mentioned above with reference to step 860, as a difference image.

Based on the image data D-Img, a step 950 calculates eye and/or gaze data D-Eye. After step 945, the procedure also loops back to step 905 in order to register another frame of image data D-Img, and thus run through another first and second set of intervals wherein the eye E is illuminated by the first and second light sources 121 and 122.

It should be noted that the reset of the photodiode may be effected in other steps of the proposed procedure than in the above-described steps 920 and 935.

All of the process steps, as well as any sub-sequence of steps, described with reference to FIGS. 8 and 9 above may be controlled by means of a programmed computer apparatus. Moreover, although the embodiments of the invention described above with reference to the drawings comprise a computer apparatus and processes performed in a computer apparatus, the invention thus also extends to computer programs, particularly computer programs on or in a carrier, adapted for putting the invention into practice. The program may be in the form of source code, object code, a code intermediate source and object code such as in partially compiled form, or in any other form suitable for use in the implementation of the process according to the invention. The program may either be a part of an operating system, or be a separate application. The carrier may be any entity or device capable of carrying the program. For example, the carrier may comprise a storage medium, such as a Flash memory, a ROM (Read Only Memory), for example a DVD (Digital Video/Versatile Disk), a CD (Compact Disc) or a semiconductor ROM, an EPROM (Erasable Programmable Read-Only Memory), an EEPROM (Electrically Erasable Programmable Read-Only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant processes.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

The invention claimed is:

1. An eye/gaze tracker, comprising:
   first and second light sources, each configured to illuminate an eye of a subject;
   an image registering means configured to record image data representing the eye; and
   a control unit configured to control the light sources and the image registering means, said image registering means comprises an image sensor with a plurality of photodiodes each of which is associated with first and second charge storages configured to store electric charges based on an amount of light reaching the photodiode, and at least one switch controllable to cause the electric charges to be stored in the first charge storage or the second charge storage,
   the control unit is configured to:
      control the light sources to selectively emit light towards the eye in such a manner that within an operation sequence the eye is illuminated by the first light source during at least one first interval and by the second light source during at least one second interval; and
      control the at least one switch such that the electric charges are stored in the first charge storage as a result of the illumination during the at least one first interval and in the second charge storage as a result of the illumination during the at least one second interval; and
   said control unit comprising a data processor configured to:
      process image data recorded by the image registering means, which image data have been registered when the eye is illuminated by light from one of the light sources; and based thereon
      generate an output signal describing at least one of a position of the eye and a gaze point for the eye.

2. The eye/gaze tracker according to claim 1, comprising a third light source configured to illuminate the eye of the subject, and the control unit is configured to:

control the light sources to selectively emit light towards the eye in such a manner that within an operation sequence the eye is illuminated by the first light source during the at least one first interval, and by one of the second and third light sources during at least one second interval; and control the at least one switch such that the electric charges are stored in the first charge storage as a result of the illumination during the at least one first interval and in the second charge storage as a result of the illumination during the at least one second interval.

3. The eye/gaze tracker according to claim 1, wherein the control unit is configured to illuminate the eye and register the image data according to a periodic scheme defining:

a respective sequence of illumination intervals when each of the light sources shall be active and passive respectively, and an operation routine for the image registering means being synchronized to the sequence of illumination intervals such that a first portion of the image data recorded when the eye is illuminated by the first light source is separated from a second portion of the image data recorded when the eye is illuminated by the second light source.

4. The eye/gaze tracker according to claim 3, wherein:
the data processor is configured to derive an image quality metric describing a quality level of the image data recorded in a given interval of the at least one first or second interval, and the control unit is configured to produce the output signal exclusively based on image data having an image quality metric exceeding a predetermined quality threshold.

5. The eye/gaze tracker according to claim 3, wherein the periodic scheme defines a first sequence of illumination intervals during which the first light source shall be active, and a second sequence of illumination intervals during which the second light source shall be active; the first sequence of intervals is temporally interleaved with the second sequence of intervals, and the control unit is configured to read out the image data after that at least one of the light sources has been activated at least two times.

6. The eye/gaze tracker according to claim 1, wherein the light sources are arranged at a distance to the image registering means and a stipulated operating distance between the eye/gaze tracker and the eye such that the light emitted from each of the light sources is expected to cause a dark-pupil effect in the image data representing the eye.

7. The eye/gaze tracker according to claim 1, wherein:
a first light source of the light sources is arranged at a distance to the image registering means and a stipulated operating distance between the eye/gaze tracker and the eye such that the light emitted from the first light source is expected to cause a bright-pupil effect in the image data representing the eye; and a second light source of the light sources is arranged at a distance to the image registering means and a stipulated operating distance between the eye/gaze tracker and the eye such that the light emitted from the second light source is expected to cause a dark-pupil effect in the image data representing the eye.

8. The eye/gaze tracker according to claim 1, wherein:
a first light source of the light sources is configured to emit light at a first center wavelength; and a second light source of the at least two light sources is configured to emit light at a second center wavelength which is separated from the first center wavelength by at least 60 nm.

9. The eye/gaze tracker according to claim 8, wherein
the first and second light sources are implemented in a common illuminator unit tunable, in response to a wavelength control signal, to generate the light at the first center wavelength as well as the light at the second center wavelength, and the control unit is arranged to generate the wavelength control signal such that it is configured to cause the common illuminator unit to generate light at the first center wavelength during the at least one first interval and generate light at the second center wavelength during the at least one second interval, and provide the common illuminator with the wavelength control signal.

10. The eye/gaze tracker according to claim 1, wherein the operation sequence corresponds to an exposure time for one frame of a moving-image sequence recorded by the image registering means.

11. The eye/gaze tracker according to claim 1, wherein the data processor is configured to:
process image data recorded by the image registering means, which image data have been registered when the eye is illuminated by light from two or more of the light sources; and based thereon generate an output signal describing at least one of a position of the eye and a gaze point for the eye.

12. The eye/gaze tracker according to claim 1, wherein the eye/gazer tracker is comprised in a portable computing device.

13. The eye/gaze tracker according to claim 1, wherein the eye/gazer tracker is comprised in a motor vehicle.

14. A method of tracking the position of an eye and/or a gaze point of a subject, comprising:
illuminating the eye of the subject with light from first and second light sources; and recording image data representing the eye by means of an image registering means, wherein the image registering means comprises an image sensor with a plurality of photodiodes each of which is associated with first and second charge storages configured to store electric charges based on an amount of light reaching the photodiode, and at least one switch controllable to cause the electric charges to be stored in the first charge storage or the second charge storage;

controlling the light sources to selectively emit light towards the eye in such a manner that within an operation sequence the eye is illuminated by the first light source during at least one first interval and by the second light source during at least one second interval;

controlling the at least one switch such that the electric charges are stored in the first charge storage as a result of the illumination during the at least one first interval and in the second charge storage as a result of the illumination during the at least one second interval;

processing image data recorded by the image registering means, which image data have been registered when the eye is illuminated by light from one of the light sources; and based thereon generating an output signal describing at least one of a position of the eye and a gaze point for the eye.

15. The method according to claim 14, comprising:
deriving an image quality metric describing a quality level of the image data recorded in a given interval of the at least one first or second interval; and producing the output signal exclusively based on image data having an image quality metric exceeding a predetermined quality threshold.

16. The method according to claim 14 further comprising illuminating the eye and registering the image data according to a periodic scheme defining:

a respective sequence of illumination intervals when each of the light sources shall be active and passive respectively, and an operation routine for the image registering means being synchronized to the sequence of illumination intervals such that a first portion of the image data recorded when the eye is illuminated by the first light source is separated from a second portion of the image data recorded when the eye is illuminated by the second light source.

17. The method according to claim 16, wherein the periodic scheme defines a first sequence of illumination intervals during which the first light source shall be active, and a second sequence of illumination intervals during which the second light source shall be active; the first sequence of intervals is temporally interleaved with the second sequence of intervals, and the method comprising reading out the image data after having activated at least one of the light sources at least two times.

18. The method according to claim 14, wherein the first and second light sources are implemented in a common illuminator unit tunable, in response to a wavelength control signal, to generate light centered at a first center wavelength as well as light centered at a second center wavelength which is separated from the first center wavelength by at least 60 nm, and the method comprises:

generating the wavelength control signal such that it is configured to cause the common illuminator unit to generate light at the first center wavelength during the at least one first interval and generate light at the second center wavelength during the at least one second interval; and providing the common illuminator with the wavelength control signal.

19. The method according to claim 14, wherein the operation sequence corresponds to an exposure time for one frame of a moving-image sequence recorded by the image registering means.

20. The method according to claim 14, wherein the data processor is configured to:

process image data recorded by the image registering means, which image data have been registered when the eye is illuminated by light from two or more of the light sources; and based thereon generate an output signal describing at least one of a position of the eye and a gaze point for the eye.

21. A computer program product stored on a non-transitory computer readable medium, comprising software instructions for operation by a computer controller, said instructions comprising:

instructions for illuminating the eye of the subject with light from first and second light sources; and instructions for recording image data representing the eye by means of an image registering means, wherein the image registering means comprises an image sensor with a plurality of photodiodes each of which is associated with first and second charge storages configured to store electric charges based on an amount of light reaching the photodiode, and at least one switch controllable to cause the electric charges to be stored in the first charge storage or the second charge storage;

instructions for controlling the light sources to selectively emit light towards the eye in such a manner that within an operation sequence the eye is illuminated by the first light source during at least one first interval and by the second light source during at least one second interval;

instructions for controlling the at least one switch such that the electric charges are stored in the first charge storage as a result of the illumination during the at least one first interval and in the second charge storage as a result of the illumination during the at least one second interval;

instructions for processing image data recorded by the image registering means, which image data have been registered when the eye is illuminated by light from one of the light sources; and based thereon instructions for generating an output signal describing at least one of a position of the eye and a gaze point for the eye.

* * * * *